US00PP34132P3

(12) United States Plant Patent
Hartmann

(10) Patent No.: US PP34,132 P3
(45) Date of Patent: Apr. 19, 2022

(54) BLUEBERRY PLANT NAMED 'CAU-01'

(50) Latin Name: ***Vaccinium* (interspecific crosses of *V. australe, V. darrowi, V. ashei* and *V. corymbosum*)**
Varietal Denomination: CAU-01

(71) Applicant: Daniel P. Hartmann, South Haven, MI (US)

(72) Inventor: Daniel P. Hartmann, South Haven, MI (US)

(73) Assignee: Daniel P. Hartmann, South Haven, MI (US)

( * ) Notice: Subject to any disclaimer, the term of this patent is extended or adjusted under 35 U.S.C. 154(b) by 0 days.

(21) Appl. No.: 16/941,986

(22) Filed: Jul. 29, 2020

(65) Prior Publication Data

US 2022/0039307 P1 Feb. 3, 2022

(51) Int. Cl.
*A01H 5/08* (2018.01)
*A01H 6/36* (2018.01)

(52) U.S. Cl.
USPC ..... Plt./157
CPC ..... *A01H 6/368* (2018.05); *A01H 5/08* (2013.01)

(58) Field of Classification Search
USPC ..... Plt./157
CPC ..... A01H 5/08
See application file for complete search history.

*Primary Examiner* — Kent L Bell
(74) *Attorney, Agent, or Firm* — Hueschen and Sage

(57) ABSTRACT

A new and distinct low-chilling blueberry plant (*Vaccinium*) variety named 'CAU-01'. The parents of 'CAU-01' are 'O'Neal' (male parent) and 'Sharpblue' (female parent), inter-specific hybrids of several species. 'CAU-01' is (a) free flowering without the use of growth regulating chemicals, (b) has a very low chilling requirement, (c) has strong resistance to fungal diseases, and (d) very early fruiting over a five (5) week period.

3 Drawing Sheets

Latin name: *Vaccinium* (interspecific crosses of *V. australe, V. darrowi, V ashei* and *V. corymbosum*).

Variety denomination: Blueberry plant named 'CAU-01'.

BACKGROUND OF THE INVENTION

Blueberry plants are perennial flowering plants with blue or purple berries. Blueberries are a well-known fruit enjoyed by many throughout the world.

The present invention relates to a blueberry plant variety 'CAU-01'.

The closest known varieties of blueberry plant are its male parent 'O'Neal' (unpatented) and its female parent 'Sharpblue' (unpatented), both interspecific hybrids.

The variety 'CAU-01' was bred by the inventor, observed and tested in Grand Junction, Mich., USA.

*Vaccinium* hybrid 'CAU-01' was derived from a controlled hybrid cross with commercial varieties 'O'Neal' (male) and 'Sharpblue' (female). Plants were hybridized in Grand Junction, Mich. USA in May 2007 and testing resumed of the variety from that date until the present.

The present cultivar, 'CAU-01', provides one or more advantages compared to the parental and/or other blueberry varieties.

BRIEF SUMMARY OF THE INVENTION

The following is a summary of the description of the new and distinct variety of blueberry 'CAU-01', its flower, fruit, stems, and foliage based on observations of specimens grown in Grand Junction, Mich. USA and Michoacan, Mexico.

*Vaccinium* hybrid 'CAU-01' was derived from un-emasculated hybrids. The hybrid parents of 'CAU-01' are 'O'Neal' used as the male parent and 'Sharpblue' used as the female parent. The plants of 'O'Neal' (male parent) and 'Sharpblue' (female parent) were hybridized in May 2007 in Grand Junction, Mich. USA. The flowers of the Female parent 'Sharpblue' were emasculated to remove all anthers and petal to obtain a true hybrid cross with the male parent 'O'Neal'. Controlled selection of pollen was inserted by hand on an emasculated female flower part. The fruit was allowed to become overripe and the seeds inside the fruits were harvested. 'CAU-01' was asexually reproduced by tissue culture and softwood cuttings in Grand Junction, Mich., USA, and cultivated in an area in Grand Junction, Mich., USA. The explant used in the tissue culture propagation process was derived from the original plant of 'CAU-01'. The plants so propagated have shown that the unique features of this new *Vaccinium* variety are stable and reproduce true to type in successive generations of asexual propagation.

'CAU-01' is free flowering without the use of growth regulating chemicals in areas with low or no chilling temperatures 'CAU-01' is a multi-stemmed, erect shrub. Branches are spreading when young. Branches are strong and upright when the plants are mature. The mature branches attain a height of 4.2 to 5 feet (1.28 to 1.5 meters) depending upon growing conditions.

'CAU-01' has a low chilling requirement compared to most commercial *Vaccinium* varieties. Ripening of fruits are very early. Fruits may be harvested in climates such as the climate of Michoacan, Mexico beginning in November. By comparison, other commercial varieties grown in Michoacan, Mexico ripen in December and January, with many of the varieties ripening in March and April.

Fruit quality is firm with a firmness scoring 8.5 on a scale of 1 to 10. The picking scar where the stern is separated from the berry is dry and is scored as 9 on a scale of 1 to 10. The fruits are suitable for fresh markets, and can be stored up to 22 days at temperatures 34 degrees F. (1.1 degrees C.).

The 'CAU-01' plant shows high resistance to *Phytophthera cinnamomii, Botryosphaeria dothidia, Gloeosporium minus, Septoria albopunctata*, and *Goleocercospora inconspicua*.

BRIEF DESCRIPTION OF THE DRAWINGS

The accompanying photographs illustrate the overall appearance of the new and distinct variety of 'CAU-01' based on observation of specimens grown at Grand Junction, Mich. USA and Low Reyes Michoacan Mexico. The age of the plants described in the drawings is three (3) years.

DETAILED BOTANICAL DESCRIPTION

Figure 1:
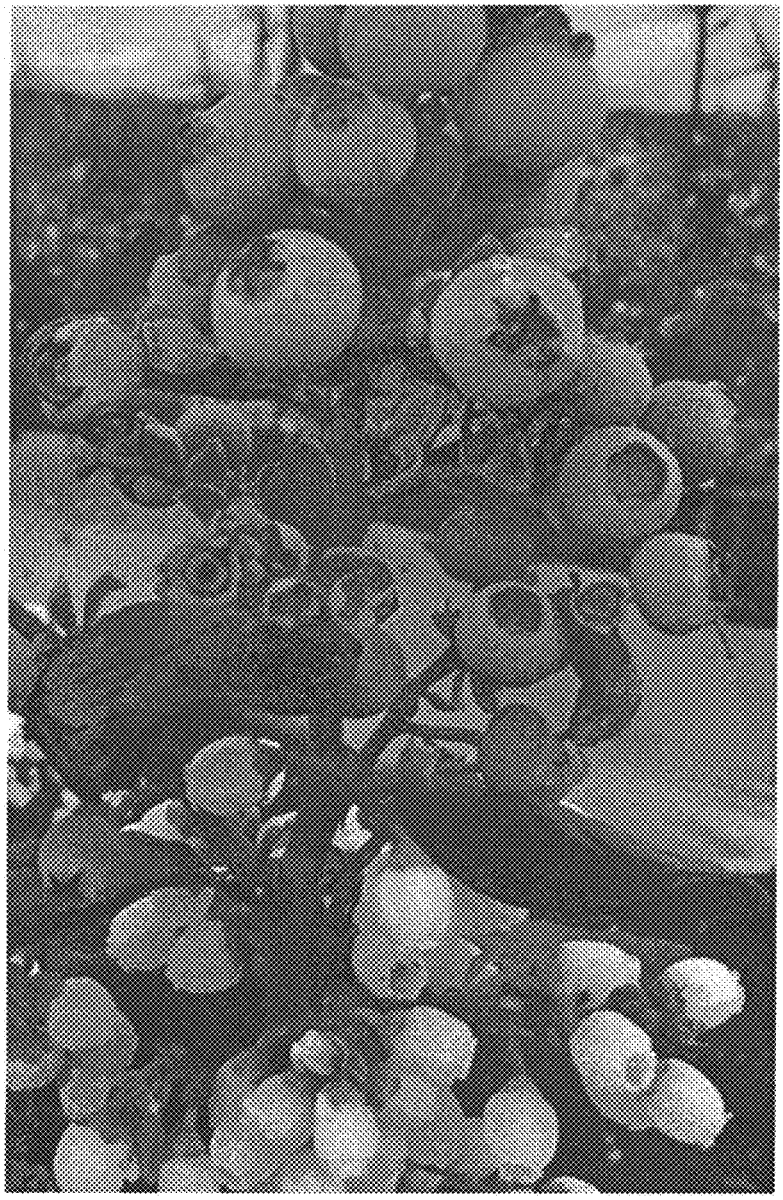
FIG. 1 is a photograph which depicts full bloom and unripe fruit clusters of the plant, as well as the upper leaf surfaces and the arrangement of the leaves on a shoot. The blossom end of the fruit with the crown-shaped calyx and pointed protrusions are depicted.
Figure 2:
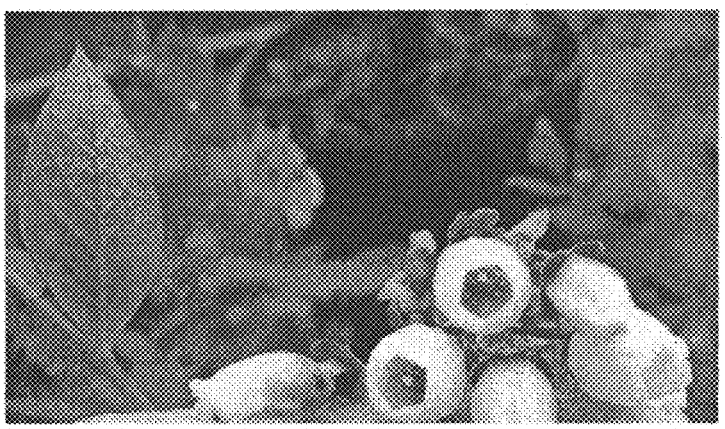
FIG. 2 shows, at close range, the color and shape of opened and un-opened flowers and the color of the peduncle and pedicel. Also shown is the leaf form and leaf venation of the plants.
Figure 3:
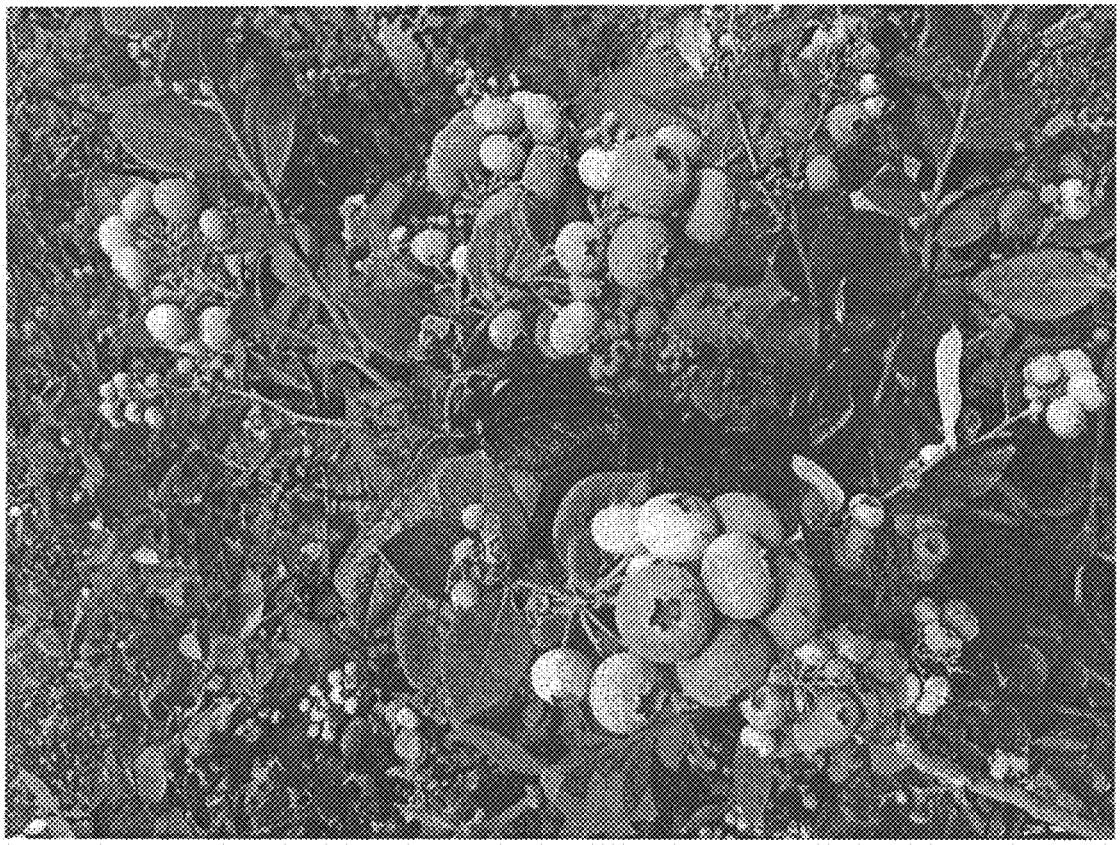
FIG. 3 is a close-up photograph of the ripe and immature fruit of 'CAU-01' showing their shape, color and amount of waxy bloom, the pedicel length and color, the fruit cluster density, mature leaves and their shape and color.

The following is a detailed botanical description of the new and distinct variety of blueberry plant, its flower, fruit, foliage and stems, based on observation of specimens grown at Grand Junction, Mich. USA and Los Reyes, Michoacan, Mexico.

Statements of characteristics herein represent exemplary observations of the cultivar herein. Where dimensions, sizes, colors, and other characteristics are given, it is to be understood that such characteristics are approximations and averages. The field observations reported herein are largely based on observations made on mature 3-year old plants located in plots in Grand Junction, Mich., USA and Los Reyes, Michoacan, Mexico. The bushes in the advanced trials were propagated from the original bush and have retained the characteristics of the original selection.

Cultivar name.—'CAU-01'.

Family.—Ericaceae.

Botanical name.—*Vaccinium* (complex ancestry, based largely on *V. australe, V. darrowi, V. ashei* and *V. corymbosum*).

Common name.—Blueberry.

Parentage: Female parent.—'Sharpblue'. Male parent.—'O'Neal'.

Color descriptions, except those given in common terms, use designations cited from The Royal Horticultural Society (R.H.S.) Colour Chart. Original publication date 1966, second publication date 1995. Colors in the drawings are only approximate, in cases where the colors in the drawings differ from the R.H.S. color designation given herein, the R.H.S. designation should be considered accurate.

The following measurements were from a mature plant 3 years of age and yielding fruits.

*Height of plants.*—4 feet tall.

*Diameter.*—3.5 feet.

*Trunk.*—Crown width is slightly narrow, 8 inches (20 cm) diameter.

*Trunk bark texture.*—Exfoliating as the trunks age.

*Bark color.*—The lightest color is (RHS 159-C) and (RHS 177-B).

*Suckering tendency.*—Moderate.

*Chilling requirement.*—Estimated less than 100 accumulative hours at 0° to 7° C. (32° to 45° F.) which provides high fruit yield and quality.

Leaves:

*Leaf arrangement.*—Alternate, deciduous.

*Leaf length.*—4.4 cm.

*Leaf width.*—2.5 cm.

*Leaf outer edge.*—Smooth.

*Leaf shape.*—Oblique and lanceolate at apex.

*Leaf petiole length.*—2.0 mm (very short).

*Leaf petiole diameter.*—1.0 mm.

*Leaf petiole color.*—(RHS 138-B).

*Summer color of upper leaf surface.*—Green (RHS 136-C) and glabrous.

*Summer color of bottom leaf surface.*—Greyed Green (RHS 192-C).

*Autumn color of upper leaf surface.*—Red (RHS 46-A).

*Autumn color of bottom leaf surface.*—(RHS N34 C).

*Leaf base.*—Acute.

Flowers: Flowering occurs with previous seasons leaves attached to the branches. Flower bracts are deciduous and glaucous. The flowers appear with previous season's foliage. New foliage occurs after pollination. Flowers are borne on racemes that are longer than pedicels.

*Color of the fresh anthers in flower at anthesis.*—(RHS 20 A).

*Pedicel and peduncle color.*—(RHS 144 C).

*Calyx color at anthesis.*—(RHS 144 B).

*Flowering period.*—Appears with the foliage from previous year with new foliage appearing after petal fall.

*Observed months of flowering.*—September

*Flower petal shape and size.*—Urceolate in shape, 7 mm uniform width in middle, with the calyx end being 5 mm in width.

*Petal number on inflorescence.*—16 to 22.

*Apex and margin.*—Urceolate.

*Petal texture.*—Ridged in the length.

*Sepal number.*—5.

*Sepal shape.*—Apex pointed and margin round.

*Sepal textures.*—Glaucous.

*Sepal color.*—(RHS 60-B) at apex and (RHS N138 C) at the base.

*Flower depth.*—0.9 mm.

*Flower diameter.*—7 mm. The petal color begins as a pinkish (RHS 62B) changing to pure white (RHS N155).

*Number of flowers per cluster.*—5 to 7.

*Pollen amount.*—Abundant.

*Pollen color.*—(RHS-10D).

*Pollen production per flower.*—1.2 mg/flower/day to 2.0 mg.

*Pedicel length at berry maturity.*—0.9 mm.

*Pedicel diameter.*—1 mm.

*Pedicel texture.*—Glaucous.

*Pedicel color*.—(RHS 138 C).
*Peduncle length at berry maturity*.—9-12 mm.
*Peduncle diameter*.—2-4 mm.
*Peduncle texture*.—Glaucous.
*Peduncle color*.—Bottom Peduncle (RHS 138 B); Top Peduncle (RHS N163 C).
*Bud shape*.—Cone.
*Bud length*.—0.6 mm.
*Bud diameter*.—3 mm.
*Bud texture*.—Scale.
*Bud color*.—(RHS 165-B).
*Inflorescent length*.—10.79 cm.
*Inflorescent width*.—5.08 cm.
*Style length*.—0.6 mm.
*Style color*.—(RHS 2 C).
*Ovary color*.—(RHS 11 A).

Berries:
*Berry cluster*.—Loose and open.
*Number of berries per cluster*.—5-7.
*Berry weight*.—1.2 to 1.4 grams.
*Berry height*.—24-25 mm.
*Berry width*.—30 mm.
*Berry shape*.—Round.
*Berry skin color* (*ripe on plant*).—Light blue (RHS 106 B).
*Berry skin color after bloom rubbed off*.—Dark violet blue (RHS N92 B).
*Berry quality*.—Very firm with small picking scar.
*Seed size*.—Well developed seeds average 1 mm long and 1 mm wide.
*Color of mature seeds after drying*.—Light brown (RHS 164 B).
*Internal flesh color of mature berry*.—Green-white (RHS 157 B).
*Berry firmness*.—8.5 rated on 1-10 scale, 10 being best.
*Berry flavor*.—9 rated on 1-10 scale, 10 is best.
*Berry texture*.—9 rated on 1-10 scale, 10 is best.
*Berry sweetness*.—High.
*Berry acidity*.—Low.
*Maturity date of berry*.—30% ripeness November 4$^{th}$ in Los Reyes, Michoacan, Mexico.
*First commercial harvest*.—(30% of the fruit ripe) typically November 4$^{th}$ in Los Reyes, Michoacan, Mexico.
*Last commercial harvest*.—typically December 1 in Los Reyes, Michoacan, Mexico.
*Productivity*.—Yields up to 4.2 pounds of berry per plant per year at maturity (3 years). The berries are suitable for fresh marketing and can be stored for a period of 22 days at 34 degrees F. (1.1 degrees C.).

Plant stems: Plant stems are cold tolerant to minus 16 degrees F. (minus 26.4 degrees C.). The fruit bracts are cold tolerant to minus 4 degrees F. (minus 20 degrees C.)
*Plant stem color*.—One and 2 year stems are colored green (RHS 140 B) and grayed-orange (RHS 172 B).
*Fruiting stems laterals color*.—Yellow green (RHS 144 C) mostly glabrous with some being slightly warty.
*Color of branches*.—Plants 3 or more years — Greyed-orange (RHS 165 C) and brown (RHS N200 D).
*One year stem length*.—3 and 4 feet.
*One year stem diameter*.—¼ to ⅜ inches.
*One year stem internode length*.—2.5 cm.
*One year stem color*.—(RHS 141 C).
*One year stem texture*.—Glaucous.
*Mature stem length*.—4 feet.
*Mature stem diameter*.—⅜ to ¾ inches.
*Mature stem color*.—(RHS 159 C) and (RHS 177 B) and (RHS 141 D).
*Mature stem texture*.—Woody and exfoliated.

The following ratings are on a scale of 1-10, with 7 being commercially acceptable and 10 being the best.
a. Spreading habit.—5.0.
b. Upright.—5.0.
c. Leaf to fruit ratio.—5.0.
d. Time of flower.—Early 5 is best for the climate where this cultivar is recommended.
e. Harvest.—Early 5 is best for the climate where this cultivar recommended.
f. Fruit size.—8.
g. Fruit color.—9.5.
h. Fruit firmness.—8.5.
i. Stem scar.—9.0.
j. Tightness of cluster.—9.5.
k. Foliar diseases.—10.
l. Fruit rots.—9.0.
m. Yield.—9.0.

The 'CAU-01' blueberry plants are highly resistant to diseases, insects, and mites: *Phytophthera cinnamon; Botyrosphaeria dothidia; Gloesporium minus; Septoria albopuncata; Gloeosercospora inconsipcua.*

'CAU-01' has similarities to both parents: 'O'Neal' the male parent for leaf form and 'Sharpblue' the female parent for crop yield and berry flavor. A comparison of 'CAU-01' with these two varieties is as shown below. The following ratings are on a scale of 1-10 with 10 being the best.

'O'Neal' characteristics:
*Upright growth habit*.—4 to 5 feet tall, slightly spreading 2½ to 3 feet wide.
2. *Leaf form*.—Lanceolate.
3. *Fruit quality*.—3.0.
4. *Fruit size*.—3.0.
5. *Yield*.—4.0.
6. *Prune yearly*.—Plants are vigorous.

B. 'Sharpblue' characteristics:
1. *Upright*.—4 to 5 feet tall, spreading to 4 feet wide.
2. *Leaf form*.—Oblique and oval.
3. *Fruit quality*.—3.0.
4. *Fruit size*.—4.0.
5. *Yield*.—4.0.
6. *Prune yearly*.—Plants are vigorous.

C. 'CAU-01' characteristics:
1. *Upright*.—4 feet tall, spreading to 3.5 feet wide.
2. *Leaf form*.—Oblique and lanceolate at apex.
3. *Fruit quality*.—8.5.
4. *Fruit size*.—8.0.
5. *Yield*.—9.0.
6. *Prune yearly*.—Plants are high vigor.

The desirable features of blueberry plant variety 'CAU-01' include a combination of attributes that are outstanding in a new variety, including for example, being free flowering without the use of growth regulating chemicals, having very low chilling requirements, very early fruit ripening, resistance to blueberry fungal diseases and ripening over a five (5) week period.

'CAU-01' is characterized by its free flowering without the use of growth regulating chemicals in areas with low or no chilling temperatures.

Compared to 'Sharpblue', 'CAU-01' has very low chilling requirements and higher yields.

Range of Adaptation—'O'Neal' requires 400 chilling hours compared to 'CAU-01' with 100 hours or less. 'Sharpblue' requires 100 chilling hours compared to 'CAU-01' which requires less than 100 hours of chilling hours. Chilling hours are accumulative hours between 0°-7° C. (32°-45° F.).

'CAU-01' has a low chilling requirement compared to most commercial *Vaccinium* varieties. Ripening of fruits are very early. Fruits may be harvested in climates such as the climate of Michoacan, Mexico beginning in November. By comparison, other commercial varieties grown in Michoacan, Mexico ripen in December and January, with many of the varieties ripening in March and April.

Compared to 'Biloxi' (unpatented), 'CAU-01' exhibits very early fruit ripening, and ripening over a five (5) week period whereas 'CAU-01' is early with concentrated ripening of the fruits with superior fruit quality of 'Biloxi'.

First fruits begin ripening 10 days earlier than one of the leading low chill commercial cultivars 'Sharpblue'.

Compared to 'Sharpblue', 'CAU-01' is highly resistant to blueberry fungal diseases, insects, and mites selected from *Phytophthera cinnamon Botyrosphaeria dothidia; Gloesporium minus; Septoria albopuncata*; and *Gloeosercospora inconsipcua*. 'Sharpblue' has no resistance to *Septoria albopuncata, Gloesporium minus* or *Phytophthera cinnamon*. 'Biloxi' is slightly resistant to *Gloesporium minus.*

What is claimed is:

1. A new and distinct variety of blueberry plant named 'CAU-01' substantially as illustrated and described herein.

* * * * *